United States Patent
Schirmer

(10) Patent No.: US 10,703,727 B2
(45) Date of Patent: Jul. 7, 2020

(54) METHOD FOR PREPARING SUBSTITUTED 3-(2-ANILINO-1-CYCLOHEXYL-1H-BENZIMIDAZOL-5-YL)PROPANOIC ACID DERIVATIVES

(71) Applicant: Bayer Pharma Aktiengesellschaft, Berlin (DE)

(72) Inventor: Heiko Schirmer, Solingen (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/748,027

(22) PCT Filed: Jul. 25, 2016

(86) PCT No.: PCT/EP2016/067614
§ 371 (c)(1),
(2) Date: Jan. 26, 2018

(87) PCT Pub. No.: WO2017/017046
PCT Pub. Date: Feb. 2, 2017

(65) Prior Publication Data
US 2018/0222871 A1   Aug. 9, 2018

(30) Foreign Application Priority Data
Jul. 27, 2015 (EP) ..................................... 15178413

(51) Int. Cl.
*C07D 235/30* (2006.01)
*A61P 35/00* (2006.01)

(52) U.S. Cl.
CPC ............ *C07D 235/30* (2013.01); *A61P 35/00* (2018.01)

(58) Field of Classification Search
CPC ..................................................... C07D 235/30
See application file for complete search history.

(56) References Cited

U.S. PATENT DOCUMENTS

| | | |
|---|---|---|
| 9,951,027 B2 | 4/2018 | Rehwinkel et al. |
| 9,957,235 B2 | 5/2018 | Rehwinkel et al. |
| 10,138,226 B2 | 11/2018 | Rehwinkel et al. |
| 10,344,004 B2 | 7/2019 | Schirmer |
| 10,370,339 B2 | 8/2019 | Ring |
| 2017/0319549 A1 | 11/2017 | Rehwinkel et al. |
| 2018/0170882 A1 | 6/2018 | Ring et al. |
| 2018/0201585 A1 | 7/2018 | Panknin et al. |
| 2018/0207137 A1 | 7/2018 | Panknin et al. |
| 2018/0215717 A1 | 8/2018 | Panknin et al. |
| 2018/0222870 A1 | 8/2018 | Schirmer |

(Continued)

FOREIGN PATENT DOCUMENTS

| | | |
|---|---|---|
| WO | WO2010151441 A1 | 12/2010 |
| WO | WO2015121209 A1 | 8/2015 |
| WO | WO2015121210 A1 | 8/2015 |

(Continued)

OTHER PUBLICATIONS

PubChem CID 21280714, National Center for Biotechnology Information. PubChem Compound Database; CID=21280714, https://pubchem.ncbi.nlm.nih.gov/compound/21280714 (accessed Nov. 9, 2018), create date Dec. 5, 2007. (Year: 2007).*
Balss, J. et al. (2012) "Enzymatic assay for quantitative analysis of (D)-2-hydroxyglutarate," Acta Neuropathol, 124:883-891.
International Search Report and Written Opinion dated Oct. 27, 2016 for International Application No. PCT/EP2016/067614 filed Jul. 25, 2016, 9 pages.
Mohrenz, I. et al. (2013) "Isocitrate dehydrogenase 1 mutant R132H sensitizes glioma cells to BCNU-induced oxidative stress and cell death," Apoptosis, 18:1416-1425.
Osol et al. eds. (1975). Remington's Pharmaceutical Sciences, Mack Publishing Company: Easton, PA (Table of Contents Only).
Prensner, J. et al. (Mar. 2011) "Metabolism unhinged: IDH mutations in cancer," Nature Medicine, 12(3):291-293.
U.S. Appl. No. 15/520,384, filed Apr. 19, 2017, for Hartmut Rehwinkel et al. (U.S. Patent Application is not submitted herewith pursuant to the waiver of 37 C.F.R § 1.98(a)(2)(iii) issued by the Office on Sep. 21, 2004.) (Also published as US-20170319549, cited herewith).

(Continued)

*Primary Examiner* — Laura L Stockton
(74) *Attorney, Agent, or Firm* — Morrison & Foerster LLP

(57) ABSTRACT

The present invention relates to a method for preparing substituted 3-(2-anilino-1-cyclohexyl-1H-benzimidazol-5-yl)propanoic acid derivatives of the general formula (I) in which $R^1$ represents a hydrogen atom or $R^1$ represents a group selected from the series of $C_1$-$C_3$-alkyl-, $C_1$-$C_3$-alkoxy-, $C_1$-$C_3$-haloalkyl- and $C_1$-$C_3$-haloalkoxy-, $R^2$ represents a hydrogen atom or a $C_1$-$C_3$-alkyl group, $R^3$ represents a hydrogen atom or a $C_1$-$C_3$-alkyl group, $R^4$ represents a cyclohexyl group, which is optionally singly or multiply substituted by a $C_1$-$C_3$-alkyl group, and $R^5$ represents a hydrogen atom or a $C_1$-$C_6$-alkyl group; and also intermediates which may be used to prepare substituted 3-(2-anilino-1-cyclohexyl-1H-benzimidazol-5-yl)propanoic acid derivatives. The present invention also relates to a crystalline form of 3-(2-{[4-(trifluoromethoxy)phenyl]amino}-1-[(1R,5R)-3,3,5-trimethylcyclohexyl]-1H-benzimidazol-5-yl)propanoic acid, pharmaceutical compositions comprising this crystalline form, and also the use of this crystalline form for preparing a medicament for the treatment of a disease.

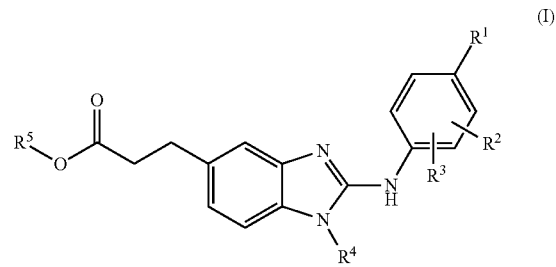

4 Claims, 1 Drawing Sheet

(56) References Cited

U.S. PATENT DOCUMENTS

2019/0062285 A1  2/2019  Rehwinkel

FOREIGN PATENT DOCUMENTS

| WO | WO2016062677 A1 | 4/2016 |
| WO | WO2016062770 A1 | 4/2016 |
| WO | WO2016198322 A1 | 12/2016 |
| WO | WO2017005674 A1 | 1/2017 |
| WO | WO2017009325 A1 | 1/2017 |
| WO | WO2017012967 A1 | 1/2017 |
| WO | WO2017016992 A1 | 2/2017 |

OTHER PUBLICATIONS

U.S. Appl. No. 15/580,372, filed Dec. 7, 2017, for Sven Ring et al. (U.S. Patent Application is not submitted herewith pursuant to the waiver of 37 C.F.R § 1.98(a)(2)(iii) issued by the Office on Sep. 21, 2004.) (Also published as US-20180170882, cited herewith).

U.S. Appl. No. 15/742,363, filed Jan. 5, 2018, for Olaf Panknin et al. (U.S. Patent Application is not submitted herewith pursuant to the waiver of 37 C.F.R § 1.98(a)(2)(iii) issued by the Office on Sep. 21, 2004.) (Also published as US-20180207137, cited herewith).

U.S. Appl. No. 15/744,641, filed Jan. 12, 2018, for Olaf Panknin et al. (U.S. Patent Application is not submitted herewith pursuant to the waiver of 37 C.F.R § 1.98(a)(2)(iii) issued by the Office on Sep. 21, 2004.) (Also published as US-20180201585, cited herewith).

U.S. Appl. No. 15/746,352, filed Jan. 19, 2018, for Olaf Panknin et al. (U.S. Patent Application is not submitted herewith pursuant to the waiver of 37 C.F.R § 1.98(a)(2)(iii) issued by the Office on Sep. 21, 2004.) (Also published as US-20180215717, cited herewith).

U.S. Appl. No. 15/748,014, filed Jan. 26, 2018, for Heiko Schirmer et al. (U.S. Patent Application is not submitted herewith pursuant to the waiver of 37 C.F.R § 1.98(a)(2)(iii) issued by the Office on Sep. 21, 2004.) (Also published as US-20180222870, cited herewith).

U.S. Appl. No. 15/923,895, filed Mar. 16, 2018, for Hartmut Rehwinkel et al. (U.S. Patent Application is not submitted herewith pursuant to the waiver of 37 C.F.R § 1.98(a)(2)(iii) issued by the Office on Sep. 21, 2004.).

* cited by examiner

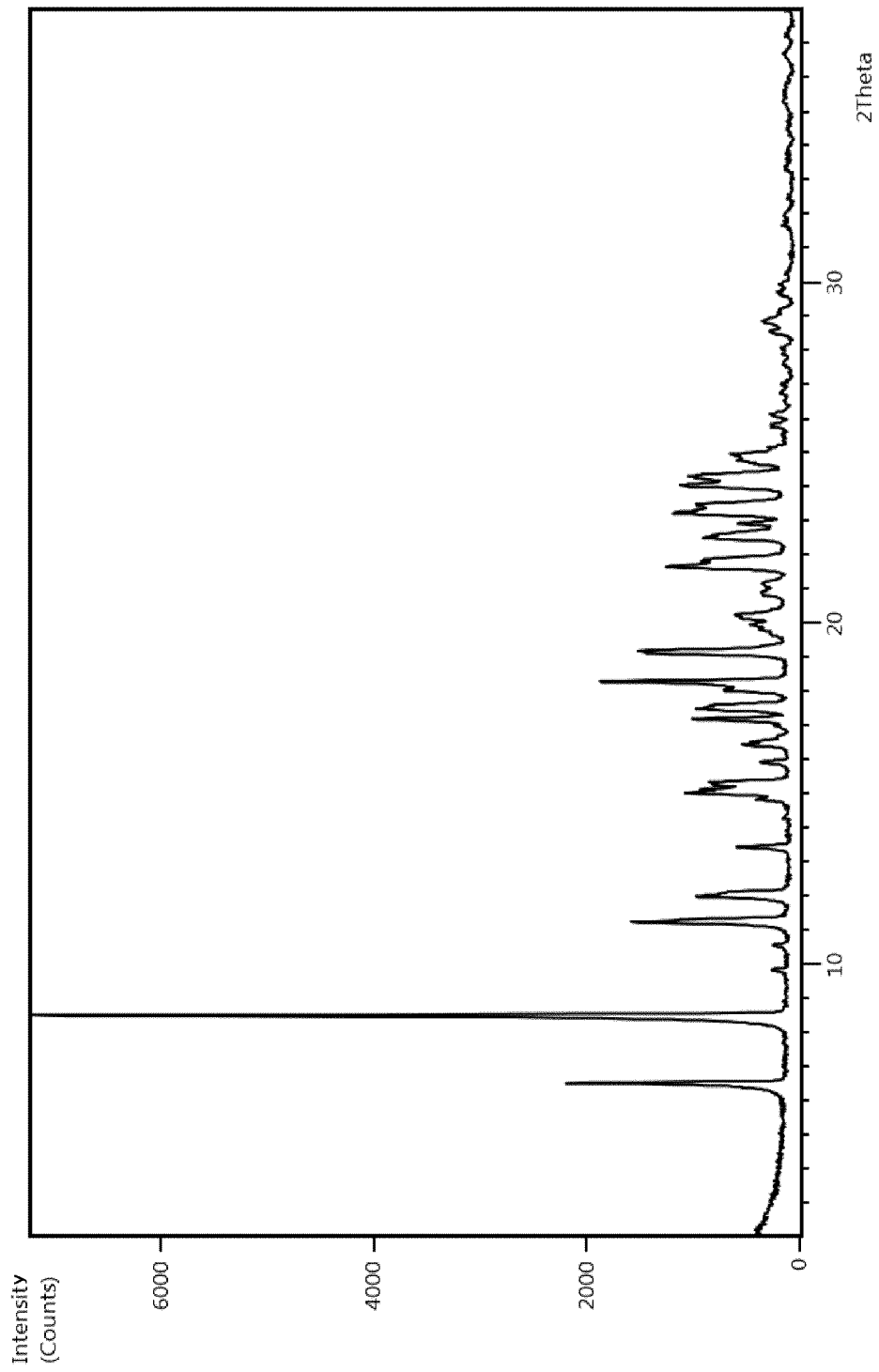

METHOD FOR PREPARING SUBSTITUTED 3-(2-ANILINO-1-CYCLOHEXYL-1H-BENZIMIDAZOL-5-YL)PROPANOIC ACID DERIVATIVES

CROSS REFERENCE TO RELATED APPLICATIONS

This application is a National Phase application under 35 U.S.C. § 371 of International Application No. PCT/EP2016/067614, filed Jul. 25, 2016, which claims priority benefit of European Application No. 15178413.9, filed Jul. 27, 2015.

The present invention relates to methods for preparing substituted 3-(2-anilino-1-cyclohexyl-1H-benzimidazol-5-yl)propanoic acid derivatives and also intermediates which may be used to prepare substituted 3-(2-anilino-1-cyclohexyl-1H-benzimidazol-5-yl)propanoic acid derivatives. The present invention also relates to a crystalline form of 3-(2-{[4-(trifluoromethoxy)phenyl]amino}-1-[(1R,5R)-3,3,5-trimethylcyclohexyl]-1H-benzimidazol-5-yl)propanoic acid, pharmaceutical compositions comprising this crystalline form, and also the use of this crystalline form for preparing a medicament for the treatment of a disease.

INTRODUCTION 3-(2-Anilino-1-cyclohexyl-1H-benzimidazol-5-yl)propanoic acid is disclosed in the published specification WO2015/121210(A1) as an inhibitor of the mutated isocitrate dehydrogenase IDH1 R132H.

IDH1 R132H is involved in various cellular processes such as the citrate cycle, lipid metabolism, repair processes such as histone methylation and DNA methylation (Prensner, J. R., and Chinnaiyan, A. M.: Metabolism unhinged: IDH mutations in cancer, Nature Medicine 2011, 17, 291-293). The inhibition of the IDH1 mutation represents a promising therapy in the treatment of tumours.

WO2010/151441(A1) discloses 4-(1-cyclopentyl-1H-benzo[d]imidazol-2-ylamino)-N-hydroxybenzamide and a method for preparing this compound.

Proceeding from this prior art, the object consisted of providing a method for preparing 3-(2-anilino-1-cyclohexyl-1H-benzimidazol-5-yl)propanoic acid, by which the 3-(2-anilino-1-cyclohexyl-1H-benzimidazol-5-yl)propanoic acid may be obtained in high yield and high purity and which may be used as an industrial production process.

DESCRIPTION OF THE INVENTION

The present invention relates to a method for preparing a compound of the general formula (I):

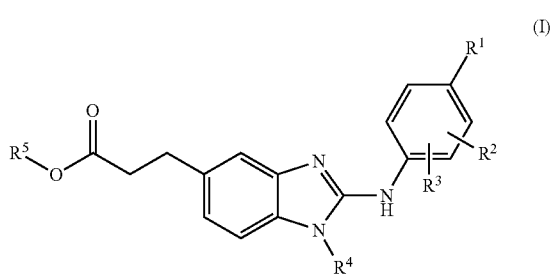

in which
$R^1$ represents a hydrogen atom or $R^1$ represents a group selected from the series of $C_1$-$C_3$-alkyl-, $C_1$-$C_3$-alkoxy-, $C_1$-$C_3$-haloalkyl- and $C_1$-$C_3$-haloalkoxy-, $R^2$ represents a hydrogen atom or a $C_1$-$C_3$-alkyl group,
$R^3$ represents a hydrogen atom or a $C_1$-$C_3$-alkyl group,
$R^4$ represents a cyclohexyl group, which is optionally singly or multiply substituted by a $C_1$-$C_3$-alkyl group, and
$R^5$ represents a hydrogen atom or a $C_1$-$C_6$-alkyl group;
wherein the method comprises a step in which a compound of the general formula (II):

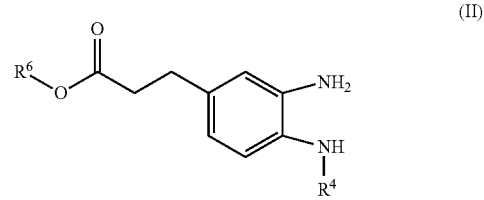

in which $R^4$ has the same definition as for the compound of formula (I) and $R^6$ represents a $C_1$-$C_6$-alkyl group, or a salt or a solvate or a solvate of a salt of the compound of the general formula (II);
is reacted with a compound of the general formula (III):

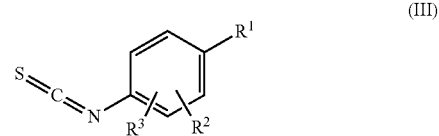

in which $R^1$, $R^2$ and $R^3$ have the same definition as for the compound of the formula (I);
and in this reaction a compound of the general formula (IV) is formed:

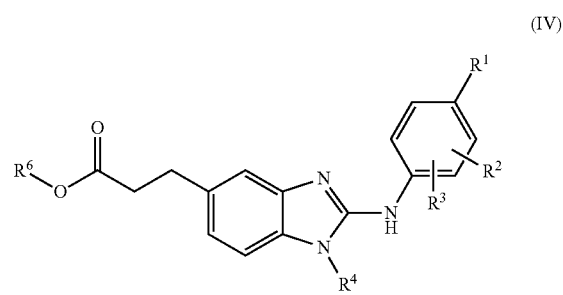

in which $R^1$, $R^2$, $R^3$ and $R^4$ have the same definition as for the compound of the formula (I) and $R^6$ has the same definition as for the compound of the formula (II).

The term "substituted" signifies that one or more hydrogens on the designated atom or the designated group has/have been replaced by a selection from the group specified, with the proviso that the normal valency of the designated atom is not exceeded under the circumstances in question. Combinations of substituents and/or variables are permissible.

The term "halogen atom" refers to a fluorine, chlorine, bromine or iodine atom, preferably a fluorine, chlorine or bromine atom.

The term "$C_1$-$C_6$-alkyl" refers to a straight-chain or branched saturated monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neopentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group or an isomer thereof. The group preferably has 1, 2, 3 or 4 carbon atoms ("$C_1$-$C_4$-alkyl"), e.g. a methyl, ethyl, propyl, isopropyl, butyl, sec-butyl, isobutyl or tert-butyl group, especially preferably 1, 2 or 3 carbon atoms ("$C_1$-$C_3$-alkyl"), e.g. a methyl, ethyl, n-propyl or isopropyl group.

The term "$C_1$-$C_3$-haloalkyl" refers to a straight-chain or branched saturated monovalent hydrocarbon group, in which the term "$C_1$-$C_3$-alkyl" is as defined above, and in which one or more of the hydrogen atoms have been replaced by the same or different halogen atoms. The halogen atom is preferably fluorine. The $C_1$-$C_3$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_3$-alkoxy" refers to a straight-chain or branched saturated monovalent group of the formula ($C_1$-$C_3$-alkyl)-O—, in which the term "$C_1$-$C_3$-alkyl" is as defined above, e.g. a methoxy, ethoxy, n-propoxy or isopropoxy group.

The term "$C_1$-$C_3$-haloalkoxy" refers to a straight-chain or branched saturated monovalent $C_1$-$C_3$-alkoxy group, as defined above, in which one or more of the hydrogen atoms has been replaced by the same or different halogen atoms. The halogen atom is in particular fluorine. The $C_1$-$C_3$-haloalkoxy group is, for example, fluoromethoxy, difluoromethoxy, trifluoromethoxy, 2,2,2-trifluoroethoxy or pentafluoroethoxy.

The term "$C_1$-$C_3$", as it is used in this text, e.g. in the context of the definition of "$C_1$-$C_3$-alkyl", "$C_1$-$C_3$-haloalkyl", "$C_1$-$C_3$-alkoxy" or "$C_1$-$C_3$-haloalkoxy", refers to an alkyl group having a number of carbon atoms limited to 1 to 3, i.e. 1, 2 or 3 carbon atoms.

If a range of values is listed, this includes every individual value and subranges within the range. For example, "$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$ and $C_5$-$C_6$.

For instance, the term "leaving group", as it is used here, refers to an atom or a group of atoms which is/are displaced, together with the binding electrons, as stable species in a chemical reaction. A leaving group is preferably selected from the group comprising: halide, particularly fluoride, chloride, bromide or iodide, (methylsulphonyl)oxy, [(trifluoromethyl)sulphonyl]oxy, [(nonafluorobutyl)sulphonyl]oxy, (phenylsulphonyl)oxy, [(4-methylphenyl)sulphonyl]oxy, [(4-bromophenyl)sulphonyl]oxy, [(4-nitrophenyl)sulphonyl]oxy, [(2-nitrophenyl)sulphonyl]oxy, [(4-isopropylphenyl)sulphonyl]oxy, [(2,4,6-triisopropylphenyl)sulphonyl]oxy, [(2,4,6-trimethylphenyl)sulphonyl]oxy, [(4-tert-butylphenyl)sulphonyl]oxy and [(4-methoxyphenyl)sulphonyl]oxy.

The reaction of a compound of the formula (II) with a compound of the formula (III) to give a compound of the formula (IV) is preferably carried out in a solvent such as tetrahydrofuran (THF) at a temperature of 40° C. to 60° C. using a coupling reagent such as 1-(3-dimethylaminopropyl)-3-ethylcarbodiimide hydrochloride (EDCl).

Compounds of the formula (II) can also be obtained by reduction of the nitro compounds of the formula (V):

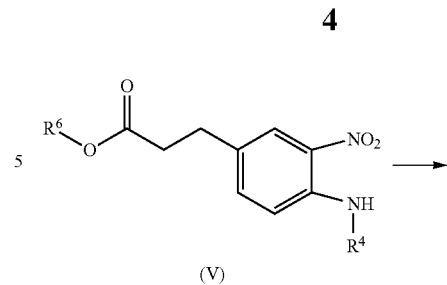

(V)

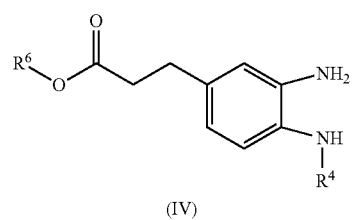

(IV)

The reduction may be carried out by way of example with gaseous hydrogen using a catalyst such as palladium on a carbon support (Pd/C) in a suitable solvent such as tetrahydrofuran (THF) at a temperature in the range from 10° C. to 60° C.

Nitro compounds of the formula (V) can be obtained, for example, in a nucleophilic aromatic substitution reaction according to the reaction scheme below:

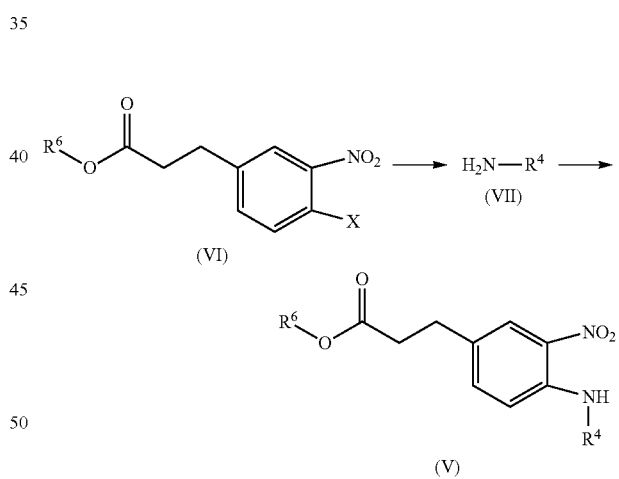

Here, X is a suitable leaving group, preferably a fluorine atom.

The nucleophilic aromatic substitution may be carried out under reflux conditions (approx. 80° C.) using a suitable base such as potassium carbonate ($K_2CO_3$) in a suitable solvent such as acetonitrile.

Compounds of the formulae (III), (VI) and (VII) are largely commercially available or may be generated from known compounds by known methods.

The acid compounds of the formula (I) can be prepared from compounds of the formula (IV) by saponification of the carboxylic ester according to the scheme below:

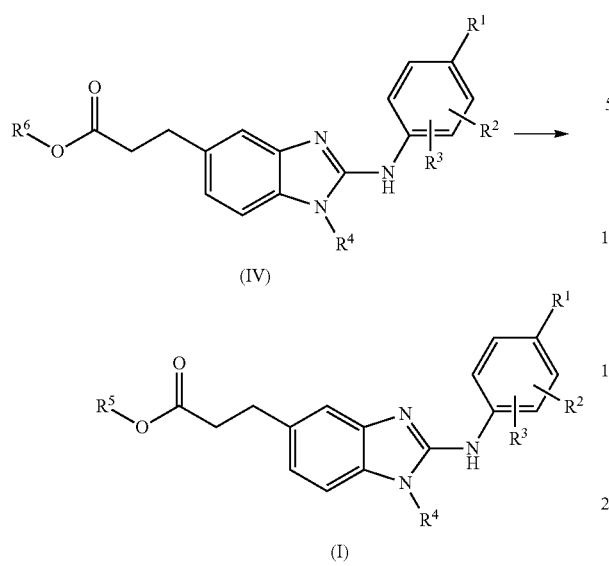

(IV)

↓

(I)

where R⁵ represents a hydrogen atom.

The saponification can be carried out, for example, by means of a base such as sodium hydroxide (NaOH) in a suitable solvent such as tetrahydrofuran (THF) at a temperature of 20° C. to 60° C.

In a preferred embodiment, $R^2$ is a hydrogen atom, $R^3$ is a hydrogen atom, while $R^1$ represents a group selected from the series of $C_1$-$C_3$-alkyl-, $C_1$-$C_3$-alkoxy-, $C_1$-$C_3$-haloalkyl- and $C_1$-$C_3$-haloalkoxy-.

In a particularly preferred embodiment, $R^2$ is a hydrogen atom, $R^3$ is a hydrogen atom, while $R^1$ represents a group selected from the series of methyl, methoxy, trifluoromethyl and trifluoromethoxy.

In an especially preferred embodiment, $R^2$ is a hydrogen atom, $R^3$ is a hydrogen atom and $R^1$ is a trifluoromethoxy group.

In a further preferred embodiment, $R^4$ represents a cyclohexyl group which is optionally mono-, di-, tri- or tetra-substituted with a methyl group.

In a particularly preferred embodiment, $R^4$ is selected from the series of:

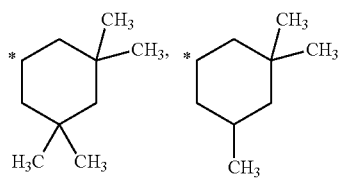

where * indicates the position where the group $R^4$ is attached to the rest of the molecule.

In a further preferred embodiment, $R^5$ represents a hydrogen atom or methyl group.

In a particularly preferred embodiment, $R^5$ represents a hydrogen atom.

In a further preferred embodiment, $R^6$ represents a methyl, ethyl, isopropyl or tert-butyl group.

In a particularly preferred embodiment, $R^6$ represents a methyl or ethyl group.

In a particularly preferred embodiment, $R^6$ represents a methyl group.

In a further particularly preferred embodiment, the method according to the invention serves to prepare a compound of the formula (Ia):

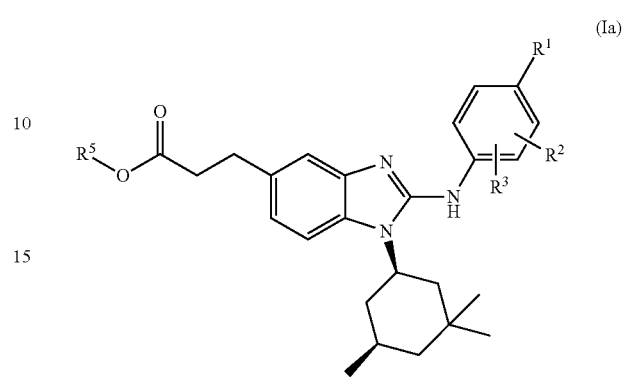

in which $R^1$ represents a hydrogen atom or $R^1$ represents a group selected from the series of $C_1$-$C_3$-alkyl-, $C_1$-$C_3$-alkoxy-, $C_1$-$C_3$-haloalkyl- and $C_1$-$C_3$-haloalkoxy-, $R^2$ represents a hydrogen atom or a $C_1$-$C_3$-alkyl group, $R^3$ represents a hydrogen atom or a $C_1$-$C_3$-alkyl group, $R^4$ represents a cyclohexyl group, which is optionally singly or multiply substituted by a $C_1$-$C_3$-alkyl group, and $R^5$ represents a $C_1$-$C_3$-alkyl group, wherein the method comprises a step in which a compound of the general formula (IIa):

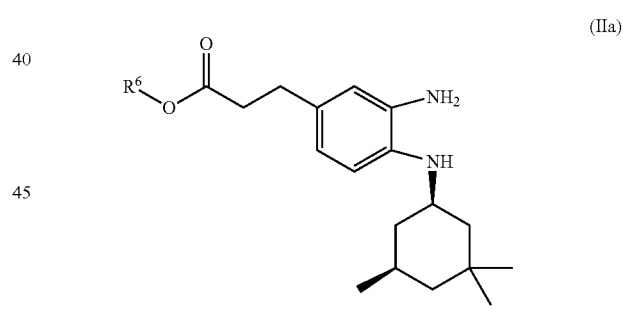

in which $R^6$ represents a $C_1$-$C_6$-alkyl group;

or a salt or a solvate or a solvate of a salt of the compound of the general formula (IIa), is reacted with a compound of the general formula (III):

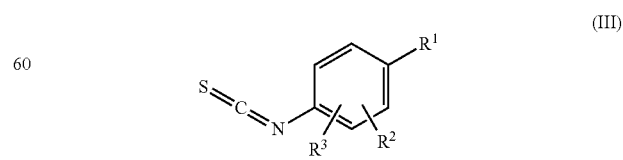

in which $R^1$, $R^2$ and $R^3$ have the same definition as for the compound of the formula (Ia);

and in this reaction a compound of the general formula (IVa) is formed:

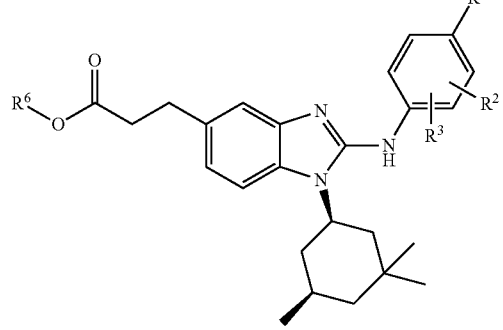
(IVa)

in which $R^1$, $R^2$ and $R^3$ have the same definition as for the compound of the formula (Ia) and $R^6$ has the same definition as for the compound of the formula (IIa).

In an especially preferred embodiment, the method according to the invention serves to prepare 3-(2-{[4-(trifluoromethoxy)phenyl]amino}-1-[(1R,5R)-3,3,5-trimethylcyclohexyl]-1H-benzimidazol-5-yl)propanoic acid, wherein the method comprises a step in which an alkyl ester of 3-(3-amino-4-{[(1R,5R)-3,3,5-trimethylcyclohexyl]amino}phenyl)propanoic acid of the formula (IIa)

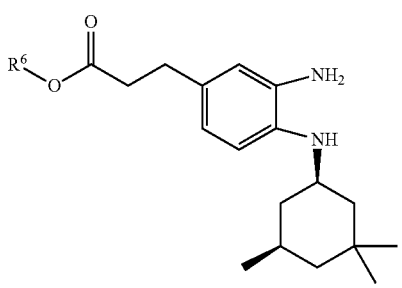
(IIa)

in which $R^6$ represents a $C_1$-$C_6$-alkyl group;

or a salt or a solvate or a solvate of a salt of the compound of the formula (IIa), is reacted with 4-isothiocyanatophenyl trifluoromethyl ether,

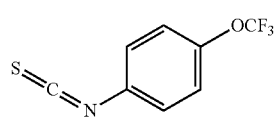 [SMILES: FC(F)(F)Oc1ccc(N=C=S)cc1]

and in this reaction an alkyl ester of 3-(2-{[4-(trifluoromethoxy)phenyl]amino}-1-[(1R,5R)-3,3,5-trimethylcyclohexyl]-1H-benzimidazol-5-yl)propanoic acid of the formula (IVa) is formed:

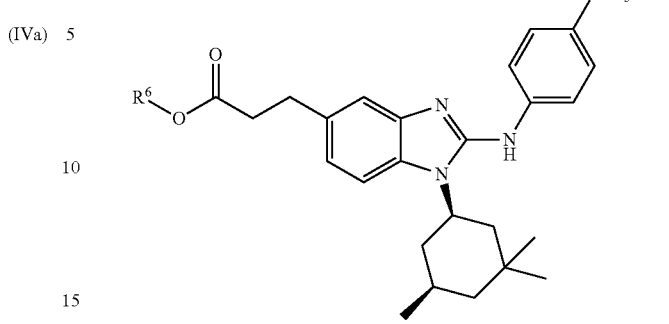
(IVa)

in which $R^6$ has the same definition as for the compound of the formula (IIa).

In a further preferred embodiment, the compound of the formula (IIa) used is the dioxane solvate of the hydrochloride of methyl 3-(3-amino-4-{[(1R,5R)-3,3,5-trimethylcyclohexyl]amino}phenyl)propanoate:

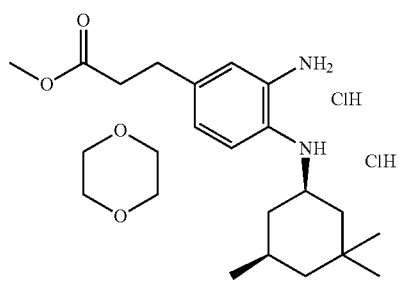

This adduct, which consists in each case of one molecule of methyl 3-(3-amino-4-{[(1R,5R)-3,3,5-trimethylcyclohexyl]amino}phenyl)propanoate, one molecule of dioxane and two molecules of hydrochloric acid, results from the treatment of methyl 3-(3-amino-4-{[(1R,5R)-3,3,5-trimethylcyclohexyl]amino}phenyl)propanoate dissolved in THF with dioxane and hydrochloric acid for example.

It can be readily purified and separated from by-products and from starting compounds which occur in the reduction of methyl 3-(3-nitro-4-{[(1R,5R)-3,3,5-trimethylcyclohexyl]amino}phenyl)propanoate to methyl 3-(3-amino-4-{[(1R,5R)-3,3,5-trimethylcyclohexyl]amino}phenyl)propanoate.

The present invention therefore further relates to methyl 3-(3-amino-4-{[(1R,5R)-3,3,5-trimethylcyclohexyl]amino}phenyl)propanoate-1,4-dioxane hydrochloride (1:1:2).

The present invention therefore further provides a method for preparing 3-(2-{[4-(trifluoromethoxy)phenyl]amino}-1-[(1R,5R)-3,3,5-trimethylcyclohexyl]-1H-benzimidazol-5-yl)propanoic acid from the starting materials alkyl ester of 3-(4-fluoro-3-nitrophenyl)propanoic acid:

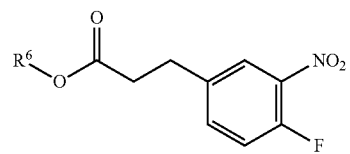

(1R,5R)-3,3,5-trimethylcyclohexanamine:

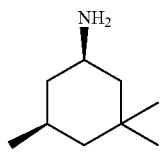

and
4-isothiocyanatophenyl trifluoromethyl ether:

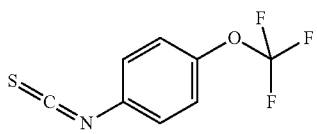

where $R^6$ represents a $C_1$-$C_6$-alkyl group.

The method according to the invention for preparing 3-(2-{[4-(trifluoromethoxy)phenyl]amino}-1-[(1R,5R)-3,3,5-trimethylcyclohexyl]-1H-benzimidazol-5-yl)propanoic acid preferably comprises the following steps:
   (a) reacting an alkyl ester of 3-(4-fluoro-3-nitrophenyl)propanoic acid with (1R,5R)-3,3,5-trimethylcyclohexanamine to give an alkyl ester of 3-(3-nitro-4-{[(1R,5R)-3,3,5-trimethylcyclohexyl]amino}phenyl)propanoic acid
   (b) reducing the alkyl ester of 3-(3-nitro-4-{[(1R,5R)-3,3,5-trimethylcyclohexyl]amino}phenyl)propanoic acid from step (a) to give an alkyl ester of 3-(3-amino-4-{[(1R,5R)-3,3,5-trimethylcyclohexyl]amino}phenyl)propanoic acid
   (c) reacting the alkyl ester of 3-(3-amino-4-{[(1R,5R)-3,3,5-trimethylcyclohexyl]amino}phenyl)propanoic acid from step (b) with 4-isothiocyanatophenyl trifluoromethyl ether to give an alkyl ester of 3-(2-{[4-(trifluoromethoxy)phenyl]amino}-1-[(1R,5R)-3,3,5-trimethylcyclohexyl]-1H-benzimidazol-5-yl)propanoic acid
   (d) saponifying the alkyl ester of 3-(2-{[4-(trifluoromethoxy)phenyl]amino}-1-[(1R,5R)-3,3,5-trimethylcyclohexyl]-1H-benzimidazol-5-yl)propanoic acid from step (c) to give 3-(2-{[4-(trifluoromethoxy)phenyl]amino}-1-[(1R,5R)-3,3,5-trimethylcyclohexyl]-1H-benzimidazol-5-yl)propanoic acid.

In a preferred embodiment, the product from step (a) is supplied to step (b) without purification.

In a further preferred embodiment, the alkyl ester of 3-(2-{[4-(trifluoromethoxy)phenyl]amino}-1-[(1R,5R)-3,3,5-trimethylcyclohexyl]-1H-benzimidazol-5-yl)propanoic acid from step (a) is treated with a hydrochloric acid/dioxane mixture in order to obtain an alkyl ester of 3-(3-amino-4-{[(1R,5R)-3,3,5-trimethylcyclohexyl]amino}phenyl)propanoic acid-1,4-dioxane hydrochloride (1:1:2), which is then supplied to step (c).

In a further preferred embodiment, the product from step (c) is supplied to step (d) without purification.

In a further preferred embodiment, the saponification in step (d) is effected by means of an aqueous sodium hydroxide solution in THF; neutralization with hydrochloric acid is then carried out and the 3-(2-{[4-(trifluoromethoxy)phenyl]amino}-1-[(1R,5R)-3,3,5-trimethylcyclohexyl]-1H-benzimidazol-5-yl)propanoic acid is crystallized out by addition of isopropanol.

The present invention further provides 3-(2-{[4-(trifluoromethoxy)phenyl]amino}-1-[(1R,5R)-3,3,5-trimethylcyclohexyl]-1H-benzimidazol-5-yl)propanoic acid in crystalline form which is obtained by treating 3-(2-{[4-(trifluoromethoxy)phenyl]amino}-1-[(1R,5R)-3,3,5-trimethylcyclohexyl]-1H-benzimidazol-5-yl)propanoic acid dissolved in THF with isopropanol (also referred to below simply as "the crystalline form").

The crystalline form, which is formed by treating the 3-(2-{[4-(trifluoromethoxy)phenyl]amino}-1-[(1R,5R)-3,3,5-trimethylcyclohexyl]-1H-benzimidazol-5-yl)propanoic acid dissolved in THF with isopropanol, can be purified more simply and effectively than the amorphous form which is produced in the method described in WO2015/121210 (A1). It has an improved pharmacological and/or pharmacokinetic profile compared to the amorphous form.

FIG. 1 shows the X-ray diffractogram of the crystalline form.

The present invention further relates to a crystalline form of 3-(2-{[4-(trifluoromethoxy)phenyl]amino}-1-[(1R,5R)-3,3,5-trimethylcyclohexyl]-1H-benzimidazol-5-yl)propanoic acid, which is characterized by maxima in the X-ray diffractogram at the following 2 theta angles: 6.5, 8.5, 11.2, 11.3, 11.9, 12.1, 13.4, 14.3, 14.8, 15.0, 15.1, 15.2, 15.3, 15.9, 16.4, 17.1, 17.4, 17.6, 18.0, 18.2, 19.1, 19.1, 19.6, 19.9, 20.1, 20.2, 20.8, 21.1, 21.6, 21.8, 22.4, 22.6, 22.9, 23.2, 23.4, 24.0, 24.3, 24.3, 24.7, 24.9.

The present invention further provides a medicament comprising 3-(2-{[4-(trifluoromethoxy)phenyl]amino}-1-[(1R,5R)-3,3,5-trimethylcyclohexyl]-1H-benzimidazol-5-yl)propanoic acid in the crystalline form specified.

The crystalline form is suitable for use as medicaments for the treatment and/or prophylaxis of diseases in humans and animals.

The pharmaceutical efficacy of the crystalline form as IDH1 R132H inhibitor can be explained by the effect of the 3-(2-{[4-(trifluoromethoxy)phenyl]amino}-1-[(1R,5R)-3,3,5-trimethylcyclohexyl]-1H-benzimidazol-5-yl)propanoic acid present.

The present invention further relates to the use of the crystalline from for the treatment and/or prophylaxis of disorders, especially for the treatment of tumours.

The present invention further provides the crystalline form for use in a method for the treatment and/or prophylaxis of tumours.

The present invention further relates to the use of the crystalline form for production of a medicament for the treatment and/or prophylaxis of disorders, especially for the treatment of tumours.

The present invention further provides a method for the treatment and/or prophylaxis of disorders, especially for the treatment of tumours, using a pharmaceutically effective amount of the crystalline form.

Solid tumours that can be treated in accordance with the invention are, for example, tumours of the breast, the respiratory tract, the brain, the reproductive organs, the gastrointestinal tract, the urogenital tract, the eye, the liver, the skin, the head and the neck, the thyroid gland, the parathyroid gland, the bones, and the connective tissue and metastases of these tumours.

Haematological tumours which can be treated are, for example,
   multiple myelomas,
   lymphomas or
   leukaemias.

Breast tumours which can be treated are, for example: breast carcinomas with positive hormone receptor status breast carcinomas with negative hormone receptor status
Her-2 positive breast carcinomas
hormone receptor and Her-2 negative breast carcinomas
BRCA-associated breast carcinomas
inflammatory breast carcinomas.

Tumours of the respiratory tract which can be treated are, for example,
non-small-cell bronchial carcinomas such as, for example, squamous cell carcinoma, adenocarcinoma, large-cell carcinoma and
small-cell bronchial carcinomas.

Tumours of the brain which can be treated are, for example,
gliomas,
glioblastomas,
astrocytomas,
meningiomas and
medulloblastomas.

Tumours of the male reproductive organs which can be treated are, for example:
prostate carcinomas,
malignant epididymal tumours
malignant testicular tumours and
penis carcinomas.

Tumours of the female reproductive organs which can be treated are, for example:
endometrial carcinomas
cervix carcinomas
ovarian carcinomas
vaginal carcinomas
vulvar carcinomas Tumours of the gastrointestinal tract which can be treated are, for example:
colorectal carcinomas
anal carcinomas
stomach carcinomas
pancreas carcinomas
oesophagus carcinomas
gall bladder carcinomas
carcinomas of the small intestine
salivary gland carcinomas
neuroendocrine tumours
gastrointestinal stroma tumours Tumours of the urogenital tract which can be treated are, for example:
urinary bladder carcinomas
kidney cell carcinomas
carcinomas of the renal pelvis and lower urinary tract Tumours of the eye which can be treated are, for example:
retinoblastomas
intraocular melanomas Tumours of the liver which can be treated are, for example:
hepatocellular carcinomas
cholangiocellular carcinomas Tumours of the skin which can be treated are, for example:
malignant melanomas
basaliomas
spinaliomas
Kaposi sarcomas
Merkel cell carcinomas Tumours of the head and neck which can be treated are, for example:
larynx carcinomas
carcinomas of the pharynx and the oral cavity
carcinomas of the middle line structures (e.g. NMC, C. A. French, Annu. Rev. Pathol. 2012, 7:247-265)

Sarcomas which can be treated are, for example:
soft tissue sarcomas
osteosarcomas Lymphomas which can be treated are, for example:
non-Hodgkin lymphomas
Hodgkin lymphomas
cutaneous lymphomas
lymphomas of the central nervous system
AIDS-associated lymphomas Leukaemias which can be treated are, for example:
acute myeloid leukaemias
chronic myeloid leukaemias
acute lymphatic leukaemias
chronic lymphatic leukaemias
hairy cell leukaemias The crystalline form can act systemically and locally. For this purpose, they can be administered in a suitable manner, for example by the oral, parenteral, pulmonary, nasal, sublingual, lingual, buccal, rectal, dermal, transdermal, conjunctival or otic route, or as implant or stent.

The crystalline form can be administered in administration forms suitable for these administration routes.

Suitable administration forms for oral administration are those which work according to the prior art, which can release the crystalline form rapidly and in a modified manner, for example tablets (uncoated or coated tablets, for example with gastric juice-resistant or retarded-dissolution or insoluble coatings which control the release of the crystalline form), tablets or films/wafers which disintegrate rapidly in the oral cavity, films/lyophilizates, capsules (for example hard or soft gelatin capsules), sugar-coated tablets, granules, pellets, powders, emulsions, suspensions or aerosols.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of suspensions, emulsions, lyophilizates or sterile powders.

Suitable administration forms for the other administration routes are, for example, pharmaceutical forms for inhalation (including powder inhalers, nebulizers), nasal drops or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The crystalline form can be converted to the administration forms mentioned. This can be accomplished in a manner known per se by mixing with inert, non-toxic, pharmaceutically suitable auxiliaries. These auxiliaries include carriers (for example microcrystalline cellulose, lactose, mannitol), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctants.

The present invention furthermore provides medicaments which comprise the crystalline form, typically together with one or more inert, nontoxic, pharmaceutically suitable auxiliaries, and the use thereof for the aforementioned purposes.

Pharmaceutical preparations are formulated in a manner known per se, by converting the active compound(s) to the desired administration form with the excipients customary in the pharmaceutical formulation.

The excipients used may, for example, be carrier substances, fillers, disintegrants, binders, humectants, glidants, absorbents and adsorbents, diluents, cosolvents, emulsifiers, taste correctors, colourants, preservatives, stabilizers, wetting agents, salts for modifying the osmotic pressure or buffers. Reference should be made to Remington's Pharmaceutical Science, 15th ed. Mack Publishing Company, East Pennsylvania (1980).

The pharmaceutical formulations can be present in solid form, for example as tablets, sugar-coated tablets, pills, suppositories, capsules, transdermal systems or in semisolid form, for example as ointments, creams, gels, suppositories, emulsions or in liquid form, for example as tinctures, suspensions or emulsions.

Auxiliaries in the context of the invention may, for example, be salts, saccharides (mono-, di-, tri-, oligo- and/or polysaccharides), proteins, amino acids, peptides, fats, waxes, oils, hydrocarbons and derivatives thereof, and the auxiliaries may be of natural origin or be obtained by synthetic or partially synthetic means.

Useful forms for oral or peroral administration are especially tablets, sugar-coated tablets, capsules, pills, powders, granules, pastilles, suspensions or emulsions.

Useful forms for parenteral administration are especially suspensions and emulsions.

The crystalline form can be used alone or, if required, in combination with one or more other pharmacologically active substances, provided that this combination does not lead to undesirable and unacceptable side effects. The present invention therefore further provides medicaments comprising the crystalline form and one or more further active compounds, especially for prophylaxis and/or treatment of the aforementioned disorders.

For example, the crystalline form may be combined with known anti-hyperproliferative, cytostatic or cytotoxic substances which are used for the treatment of neoplastic disorders, but it may also be combined at the same time with those substances having a supporting or constitutive property, or it may also be combined with those compounds which show positive effects in angiogenesis.

Suitable pharmacologically active substances which are useful for a combination, although not an exhaustive list, include for example:

131I-chTNT, abarelix, abiraterone, aclarubicin, aflibercept, aldesleukin, alemtuzumab, alitretinoin, altretamine, aminoglutethimide, amrubicin, amsacrine, anastrozole, arglabin, arsenic trioxide, asparaginase, axitinib, azacitidine, basiliximab, belotecan, bendamustine, bevacizumab, bexarotene, bicalutamide, bisantrene, bleomycin, bortezomib, bosutinib, brentuximab, buserelin, busulfan, cabazitaxel, cabozantinib-s-malate, calcium folinate, calcium levofolinate, capecitabine, carboplatin, carfilzomib, carmofur, carmustine, catumaxomab, celecoxib, celmoleukin, cediranib, cetuximab, chlorambucil, chlormadinone, chlormethine, cisplatin, cladribine, clodronic acid, clofarabine, copanlisib, crisantaspase, crizotinib, cyclophosphamide, cyproterone, cytarabine, dacarbazine, dactinomycin, darbepoetin alfa, dasatinib, daunorubicin, debrafenib, decitabine, degarelix, denileukin diftitox, denosumab, deslorelin, dexrazoxane hydrochloride, dibrospidium chloride, docetaxel, doxifluridine, doxorubicin, doxorubicin+estrone, eculizumab, edrecolomab, elliptinium acetate, eltrombopag, endostatin, enocitabine, enzalutamide, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glucarpidase, glutoxim, goserelin, histamine dihydrochloride, histrelin, hydroxycarbamide, I-125 seeds, ibandronic acid, ibritumomab tiuxetan, ibrutinib, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, leucovorin, levamisole, lisuride, lobaplatin, lomustine, lonidamine, masoprocol, mechlorethamine, medroxyprogesterone, megestrol, melphalan, mepitiostane, mercaptopurine, mesna, methotrexate, methoxsalen, methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, obinutuzumab, ofatumumab, omacetaxine mepesuccinate, omeprazole, oprelvekin, oxaliplatin, ozogamicin, p53 gene therapy, paclitaxel, palifermin, palladium-103 seed, palonosetron hydrochloride, pamidronic acid, pamidronate disodium, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, pertuzumab, picibanil, pirarubicin, plerixafor, plicamycin, poliglusam, polyestradiol phosphate, polysaccharide-K, pomalidomide, pomatinib, porfimer sodium, pralatrexate, prednimustine, prednisone, procarbazine, quinagolide, radium-223 chloride, raloxifene, raltitrexed, ramucirumab, rasburicase, ranimustine, razoxane, refametinib, regorafenib, risedronic acid, rituximab, romidepsin, romiplostim, roniciclib, ruxolitinib, sargramostim, sipuleucel-T, sizofiran, sobuzoxane, sodium glycididazole, sorafenib, streptozocin, sunitinib, talaporfin, talc, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, I 131 tositumomab, trametinib, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Generally, the following aims can be pursued with the combination of the crystalline form with other cytostatically or cytotoxically active agents:

- improved efficacy in slowing the growth of a tumour, in reducing its size or even in completely eliminating it, compared with treatment with an individual active ingredient;
- the possibility of using the chemotherapeutics used in a lower dosage than in the case of monotherapy;
- the possibility of a more tolerable therapy with fewer side effects compared with individual administration;
- the possibility of treatment of a broader spectrum of neoplastic disorders;
- the achievement of a higher rate of response to the therapy;

a longer survival time of the patient compared with present-day standard therapy.

In addition, the crystalline form can also be used in combination with radiotherapy and/or surgical intervention.

EXPERIMENTAL SECTION

Examples

Example 1

Preparation of methyl 3-(3-nitro-4-{[(1R,5R)-3,3,5-trimethylcyclohexyl]amino}phenyl)propanoate (V)

402 g (1.77 mol) of methyl 3-(4-fluoro-3-nitrophenyl)propanoate (VI) as a solution in 3.0 L of acetonitrile were initially charged with 367 g (2.66 mol) of potassium carbonate and 300 g (2.12 mol) of (1R,5R)-3,3,5-trimethylcyclohexanamine were added. The mixture was stirred for 12 hours under reflux at a jacket temperature of 100° C. After cooling to 20° C., 3.6 L of water were added to the mixture. To improve phase separation, 1.0 L of saturated sodium chloride solution was added. The lower aqueous phase was removed. The organic phase was concentrated under reduced pressure (ca. 50 mbar) at a jacket temperature of 50° C. to give an oily residue. Yield: 640.5 g (104% of theory) of a highly viscous orange oil.

$^1$H-NMR (400 MHz, DMSO-d$_6$): δ [ppm]=0.75-0.87 (m, 2H), 0.89 (d, 3H), 0.93 (s, 3H), 1.02 (s, 3H), 1.10 (t, 1H), 1.34-1.39 (m, 1H), 1.68-1.83 (m, 2H), 1.99-2.02 (m, 1H), 2.58-2.62 (m, 2H), 2.75-2.79 (m, 2H), 3.57 (s, 3H), 3.73-3.82 (m, 1H), 7.07 (d, 1H), 7.44 (dd, 1H), 7.79 (br. d., 1H), 7.89 (d, 1H).

Example 2

Preparation of methyl 3-(3-amino-4-{[(1R,5R)-3,3,5-trimethylcyclohexyl]amino}phenyl)propanoate Dihydrochloride Dioxane Solvate (IIa)

640.5 g (1.77 mol) of methyl 3-(3-nitro-4-{[(1R,5R)-3,3,5-trimethylcyclohexyl]amino}phenyl)propanoate (crude product from Example 1) as a solution in 3.2 L of tetrahydrofuran were initially charged with 32 g of palladium catalyst (5% by weight; 0.05 eq., 32 g, 88.5 mmol) in a hydrogenation reactor and the mixture was stirred under a hydrogen atmosphere (1.5 bar positive pressure) at a temperature of 25° C. for 10 h. The reaction mixture was filtered off through a pressure filter (Seitz K300 filter plate) and the filtrate was concentrated under reduced pressure (ca. 50 mbar) at a jacket temperature of 50° C. to give an oily residue. The residue was dissolved in 1.3 L of dioxane and to this was added 560 mL of 4N HCl in dioxane (4.4 mol HCl) at an internal temperature of 20° C. over a period of 20 min. In the course of this, the product crystallized out. This was stirred for 2 h, filtered off and washed twice, each time with 500 mL of MTBE. The moist product was dried in a drying cabinet at a temperature of 40° C. for 4 h under vacuum.

Yield: 785 g (91% of theory, based on use of methyl 3-(4-fluoro-3-nitrophenyl)propanoate) of a pale yellow solid.

$^1$H-NMR (400 MHz, DMSO-d$_6$): δ [ppm]=0.72-0.84 (m, 1H), 0.85-1.05 (m, 10H), 1.19-1.28 (m, 1H), 1.31-1.35 (m, 1H), 1.59-1.71 (m, 2H), 1.90-1.97 (m, 1H), 2.56-2.62 (m, 2H), 2.72-2.78 (m, 2H) 3.51-3.54 (m, 1H), 3.55 (s, 3H), 3.57 (s, 8H, dioxane), 6.28-6.37 (br. m., 5H), 6.69 (br. d., 1H), 6.70 (s, 1H), 7.01 (br. d., 1H).

Example 3

Preparation of 3-(2-{[4-(trifluoromethoxy)phenyl]amino}-1-[(1R,5R)-3,3,5-trimethylcyclohexyl]-1H-benzimidazol-5-yl)propanoic Acid (I)

To a suspension of 500 g (1.043 mol) of methyl 3-(3-amino-4-{[(1R,5R)-3,3,5-trimethylcyclohexyl]amino}phenyl)propanoate dihydrochloride dioxane solvate (IIa) in 3.0 L of THF were added 296.5 g (2.29 mol) of N,N-diisopropylethylamine at a temperature of 20° C. and the mixture was stirred for 30 min. 252 g (1.15 mol) of 4-(trifluoromethoxy)phenyl isothiocyanate were added and the temperature maintained at 50° C. for 1 h. Subsequently, 300 g (1.56 mol) of EDCl were added and the mixture was stirred for 4 h under reflux at a jacket temperature of 80° C. The mixture was cooled to 20° C., 1.5 L of 20% aqueous citric acid solution were added, the mixture stirred for 30 min, 1.5 L of MTBE were added and the mixture stirred further for 15 min. The lower aqueous phase was removed. The organic phase was extracted twice, each time with 1.5 L of 4.8% aqueous sodium hydrogen carbonate solution. The organic phase was concentrated under reduced pressure (ca. 50 mbar) at a jacket temperature of 50° C. to give an oily residue to which were subsequently added 3 L of THF and 2 L of 3.7% sodium hydroxide solution (1.56 mol), and the mixture was stirred at a temperature of 50° C. for 3 h. After cooling to 20° C., the mixture was adjusted to a pH of 4 with 10% aqueous hydrochloric acid, 500 mL of saturated sodium chloride solution were added and the aqueous phase was removed. The organic phase was concentrated at a jacket temperature of 80° C. to give an oily residue, to which 4 L of isopropanol were then added and ca. 2.5 L were distilled off at a jacket temperature of 100° C. 900 mL of water were added at the same time over a period of 20 min at an internal temperature of 80° C. In the course of this, the product crystallized out from the hot mixture. After cooling to 20° C., the product was filtered off and washed successively with 500 mL of isopropanol and 500 mL of water. The moist product was dried in a drying cabinet at a temperature of 60° C. for 16 h under vacuum.

Yield: 398 g (77% of theory) of a white crystalline solid (m.p.: 248° C.).

$^1$H-NMR (400 MHz, DMSO-d$_6$): δ [ppm]=0.93 (s, 3H), 0.96 (s, 3H), 1.03 (s, 3H), 1.04-1.12 (m, 1H), 1.35-1.44 (m, 2H), 1.70-1.92 (m, 3H), 2.03 (t, 1H), 2.43-2.60 (m, 2H), 2.85 (t, 2H), 4.63 (t, 1H), 6.90 (d, 1H), 7.24 (s, 1H), 7.32 (d, 2H), 7.42 (d, 1H), 7.79 (d, 2H), 8.98 (br. s., 1H), 12.06 (br. s., 1H).

X-Ray Powder Diffractogram

FIG. 1 shows the X-ray diffractogram of the crystalline form according to the invention.

To record the X-ray diffractogram, an automated STOE powder diffractometer was used in transmission mode using germanium-monochromatized CuKα$_1$ radiation. The X-ray tube with copper anode was operated at 40 kV and 40 mA. The 2Θ scans were recorded between 2°≤2Θ≤40° (step size 0.5°). The software STOE WinX$^{pow}$ was used to evaluate the data.

The maxima of the 2Θ values are listed in Table 1.

TABLE 1

| XRPD Band maxima [°2 θ] |
|---|
| 6.5 |
| 8.5 |
| 9.8 |
| 10.5 |
| 11.2 |
| 11.3 |
| 11.9 |
| 12.1 |
| 13.4 |
| 14.3 |
| 14.8 |
| 15.0 |
| 15.1 |
| 15.2 |
| 15.3 |
| 15.9 |
| 16.4 |
| 17.1 |
| 17.4 |
| 17.6 |
| 18.0 |
| 18.2 |
| 19.1 |
| 19.1 |
| 19.6 |
| 19.9 |
| 20.1 |
| 20.2 |
| 20.8 |
| 21.1 |
| 21.6 |
| 21.8 |
| 22.4 |
| 22.6 |
| 22.9 |
| 23.2 |
| 23.4 |
| 24.0 |
| 24.3 |
| 24.3 |
| 24.7 |
| 24.9 |
| 25.1 |
| 25.7 |
| 26.1 |
| 26.7 |
| 27.0 |
| 27.6 |
| 27.8 |
| 28.0 |
| 28.5 |
| 28.8 |
| 29.2 |
| 29.7 |
| 29.9 |
| 30.2 |
| 31.6 |
| 31.9 |
| 32.5 |
| 33.3 |
| 33.8 |
| 34.4 |
| 35.3 |
| 36.6 |
| 37.1 |

Inhibition of IDH1 R132H in a Biochemical Assay

IDH1 R132H catalyzes the NADPH-dependent reduction of alpha-ketoglutarate (α-KG) to (2R)-2-hydroxyglutarate (2-HG). NADPH consumption is determined by luminescence.

The biochemical reactions were carried out at 32° C. in a 384-well titre plate in a reaction volume of 41 μL in each case and under the following buffer conditions: 50 mM Tris pH 7.5, 100 mM NaCl, 20 mM $MgCl_2$, 0.05% BSA, 0.01% Brij, 1 μM NADPH, and 250 μM α-KG. The IDH1 R132H enzyme was used at a final concentration of 1.5 nM. Test compounds were assayed in a concentration range of 0.002 to 10 μM. The final DMSO concentration was 2.4%.

The reaction mixture was incubated for 30 minutes, after which 40 μL of a detection mixture (0.75 μg/ml luciferase, 0.02 U/ml oxidoreductase, 4 μg/mL FMN, 2 μL/ml decanal/ethanol, 50 mM Tris pH 7.5, 0.5% glycerol, 0.01% Tween 20, 0.05% BSA) were added. The luminescence was determined using a luminescence reader (10 seconds measurement time, 1 second integration period, 30% sensitivity). The drop in luminescence is proportional to the activity of mIDH1. $IC_{50}$ values were determined by interpolation from plots of the relative luminescence against the inhibitor concentration. The results are compiled in table 2.

TABLE 2

| $IC_{50}$ values of selected IDH1 R132H inhibitors | |
|---|---|
| 3-[1-(3,3,5,5-Tetramethylcyclohexyl)-2-{[4-(trifluoromethoxy)phenyl]amino}-1H-benzimidazol-5-yl]propanoic acid Example | IDH1 R132H $IC_{50}$ [μM] |
| 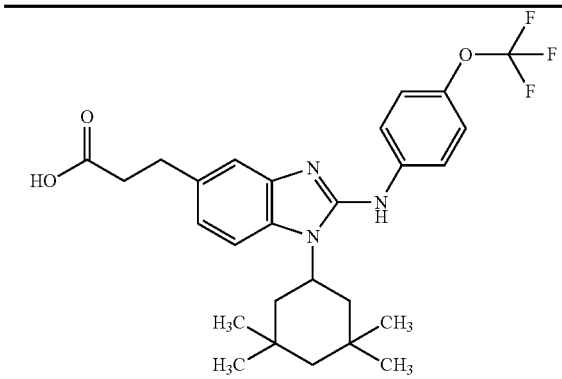 | 0.03 |

TABLE 2-continued

IC$_{50}$ values of selected IDH1 R132H inhibitors

| Example | IDH1 R132H IC$_{50}$ [μM] |
| --- | --- |
| (±) 3-(1-[3,3-Dimethylcyclohexyl]-2-{[4-(propan-2-yloxy)phenyl]amino}-1H-benzimidazol-5-yl)propanoic acid | 0.30 |
| (±) 3-(1-[3,3-Dimethylcyclohexyl]-2-{[4-(propan-2-yl)phenyl]amino}-1H-benzimidazol-5-yl)propanoic acid | 0.05 |
| 3-[2-{[4-(Propan-2-yl)phenyl]amino}-1-(3,3,5,5-tetramethylcyclohexyl)-1H-benzimidazol-5-yl]propanoic acid | 0.02 |

TABLE 2-continued

IC$_{50}$ values of selected IDH1 R132H inhibitors

| Example | IDH1 R132H IC$_{50}$ [μM] |
|---|---|
| (±) 3-(1-[3,3-dimethylcyclohexyl]-2-{[4-(trifluoromethoxy)phenyl]amino}-1H-benzimidazol-5-yl)propanoic acid | 0.06 |
| Methyl 3-[2-{[4-(propan-2-yl)phenyl]amino}-1-(3,3,5,5-tetramethylcyclohexyl)-1H-benzimidazol-5-yl]propanoate | 0.09 |
| Methyl 3-[2-{[4-(propan-2-yloxy)phenyl]amino}-1-(3,3,5,5-tetramethylcyclohexyl)-1H-benzimidazol-5-yl]propanoate | 0.43 |

TABLE 2-continued

IC$_{50}$ values of selected IDH1 R132H inhibitors

| Example | IDH1 R132H IC$_{50}$ [μM] |
|---|---|
| (±) Methyl 3-(1-[-3,3-dimethylcyclohexyl]-2-{[4-(propan-2-yl)phenyl]amino}-1H-benzimidazol-5-yl)propanoate | 0.9 |
| (±) Methyl 3-(1-[3,3-dimethylcyclohexyl]-2-{[4-(propan-2-yloxy)phenyl]amino}-1H-benzimidazol-5-yl)propanoate | 1.9 |
| (±) Methyl 3-(1-[3,3-dimethylcyclohexyl]-2-{[4-(trifluoromethoxy)phenyl]amino}-1H-benzimidazol-5-yl)propanoate | 1.7 |

TABLE 2-continued

IC$_{50}$ values of selected IDH1 R132H inhibitors

| Example | IDH1 R132H IC$_{50}$ [µM] |
| --- | --- |
| Methyl 3-[1-(3,3,5,5-tetramethylcyclohexyl)-2-{[4-(trifluoromethoxy)phenyl]amino}-1H-benzimidazol-5-yl]propanoate | 0.18 |
| (±) 3-(2-{[4-(Propan-2-yl)phenyl]amino}-1-[(cis)-3,3,5-trimethylcyclohexyl]-1H-benzimidazol-5-yl)propanoic acid | 0.02 |
| (±) 3-(2-{[4-(Propan-2-yloxy)phenyl]amino}-1-[(cis)-3,3,5-trimethylcyclohexyl]-1H-benzimidazol-5-yl)propanoic acid | 0.06 |

TABLE 2-continued

IC$_{50}$ values of selected IDH1 R132H inhibitors

| Example | IDH1 R132H IC$_{50}$ [μM] |
|---|---|
| (±) 3-(2-{[4-(Trifluoromethyl)phenyl]amino}-1-[(cis)-3,3,5-trimethylcyclohexyl]-1H-benzimidazol-5-yl)propanoic acid | 0.04 |
| (±) 3-(2-{[4-(Trifluoromethoxy)phenyl]amino}-1-[(cis)-3,3,5-trimethylcyclohexyl]-1H-benzimidazol-5-yl)propanoic acid | 0.02 |
| (±) Methyl 3-(2-{[4-(propan-2-yl)phenyl]amino}-1-[(cis)-3,3,5-trimethylcyclohexyl]-1H-benzimidazol-5-yl)propanoate | 0.17 |

TABLE 2-continued

IC$_{50}$ values of selected IDH1 R132H inhibitors

| Example | IDH1 R132H IC$_{50}$ [μM] |
|---|---|
| (±) Methyl 3-(2-{[4-(trifluoromethyl)phenyl]amino}-1-[(cis)-3,3,5-trimethylcyclohexyl]-1H-benzimidazol-5-yl)propanoate | 0.28 |

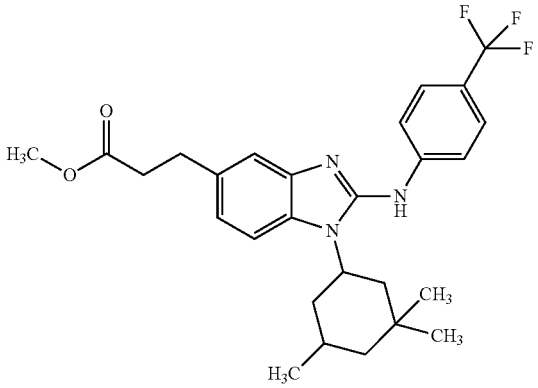 [SMILES: COC(=O)CCc1ccc2c(c1)nc(Nc1ccc(C(F)(F)F)cc1)n2C1CC(C)CC(C)(C)C1]

| (±) Methyl 3-(2-{[4-(trifluoromethoxy)phenyl]amino}-1-[(cis)-3,3,5-trimethylcyclohexyl]-1H-benzimidazol-5-yl)propanoate | 0.30 |

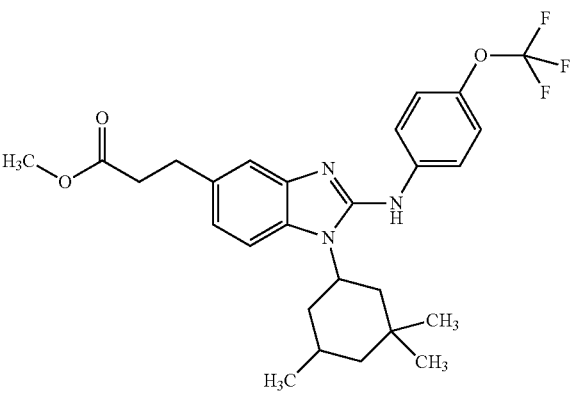 [SMILES: COC(=O)CCc1ccc2c(c1)nc(Nc1ccc(OC(F)(F)F)cc1)n2C1CC(C)CC(C)(C)C1]

Cellular Assay

Concentrations of (2R)-2-hydroxyglutarate (2HG) were determined in a medium of a cell line having an overexpession of the mutated isocitrate dehydrogenase protein. mIDH catalyses the NADPH-dependent reduction of alpha-ketoglutarate to 2-HG. Cells (LN229 R132H, Mohrenz et al., Apoptosis (2013) 18:1416-1425) were cultured in DMEM containing 10% FCS. The cells were obtained using trypsin and placed in 96-well titre plates. The cells were incubated overnight at 37° C. in 5% CO$_2$. On the next day, test compounds were added to the cells. The final concentration of DMSO was 0.1% and DMSO controls were used. The titre plates were then placed in an incubator for 24 hours.

2-HG was measured using the method published by Balss et al. (Acta Neuropathol (2012) 124: 883-891). HClO$_4$ was added to each well and the titre plates were centrifuged. Aliquots were removed and incubated with hydroxyglutarate dehydrogenase (HGDH), diaphorase, NAD+ and resazurin. The conversion of resazurin to resorufin was determined by fluorescence spectroscopy at Ex 540 nm Em 600 nm. The increase in the fluorescence signal is proportional to formation of 2-HG. IC$_{50}$ values were determined by interpolation from plots of the relative fluorescence against the inhibitor concentration. The results are compiled in table 3.

TABLE 3

Inhibition of IDH1 R132H in the cellular assay

| Example | IDH1 R132H IC$_{50}$ [μM] |
|---|---|
| 3-[1-(3,3,5,5-Tetramethylcyclohexyl)-2-{[4-(trifluoromethoxy)phenyl]amino}-1H-benzimidazol-5-yl]propanoic acid | 0.30 |
| (±) 3-(1-[3,3-Dimethylcyclohexyl]-2-{[4-(propan-2-yloxy)phenyl]amino}-1H-benzimidazol-5-yl)propanoic acid | 0.85 |
| (±) 3-(1-[3,3-Dimethylcyclohexyl]-2-{[4-(propan-2-yl)phenyl]amino}-1H-benzimidazol-5-yl)propanoic acid | 0.40 |

TABLE 3-continued

Inhibition of IDH1 R132H in the cellular assay

| Example | IDH1 R132H IC$_{50}$ [μM] |
| --- | --- |
| 3-[2-{[4-(Propan-2-yl)phenyl]amino}-1-(3,3,5,5-tetramethylcyclohexyl)-1H-benzimidazol-5-yl]propanoic acid | 0.03 |
| (±) 3-(1-[3,3-Dimethylcyclohexyl]-2-{[4-(trifluoromethoxy)phenyl]amino}-1H-benzimidazol-5-yl)propanoic acid | 0.85 |
| Methyl 3-[2-{[4-(propan-2-yl)phenyl]amino}-1-(3,3,5,5-tetramethylcyclohexyl)-1H-benzimidazol-5-yl]propanoate | 0.05 |

TABLE 3-continued
Inhibition of IDH1 R132H in the cellular assay
| Example | IDH1 R132H IC$_{50}$ [μM] |
|---|---|
| Methyl 3-[1-(3,3,5,5-tetramethylcyclohexyl)-2-{[4-(trifluoromethoxy)phenyl]amino}-1H-benzimidazol-5-yl]propanoate 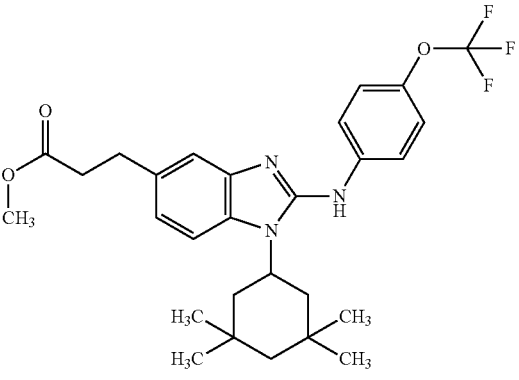 [SMILES: COC(=O)CCc1ccc2c(c1)nc(Nc1ccc(OC(F)(F)F)cc1)n2C1CC(C)(C)CC(C)(C)C1] | 0.08 |
| (±) 3-(2-{[4-(Propan-2-yl)phenyl]amino}-1-[(cis)-3,3,5-trimethylcyclohexyl]-1H-benzimidazol-5-yl)propanoic acid 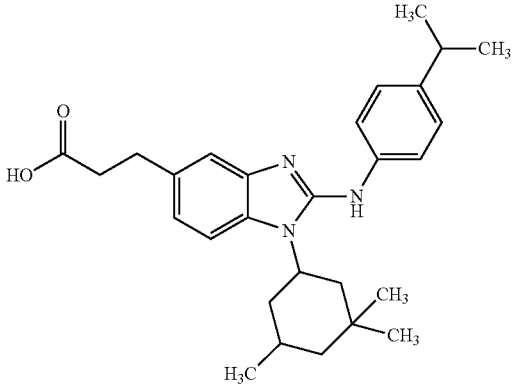 [SMILES: CC1CC(n2c(Nc3ccc(C(C)C)cc3)nc3cc(CCC(=O)O)ccc32)CC(C)(C)C1] | 0.08 |
| (±) 3-(2-{[4-(Propan-2-yloxy)phenyl]amino}-1-[(cis)-3,3,5-trimethylcyclohexyl]-1H-benzimidazol-5-yl)propanoic acid 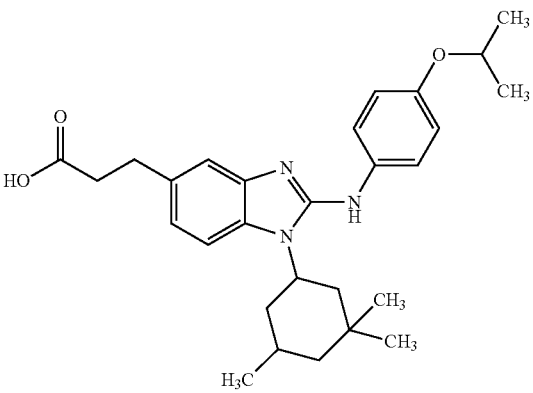 [SMILES: CC1CC(n2c(Nc3ccc(OC(C)C)cc3)nc3cc(CCC(=O)O)ccc32)CC(C)(C)C1] | 0.40 |

TABLE 3-continued
Inhibition of IDH1 R132H in the cellular assay
| Example | IDH1 R132H IC$_{50}$ [µM] |
|---|---|
| (±) 3-(2-{[4-(Trifluoromethyl)phenyl]amino}-1-[(cis)-3,3,5-trimethylcyclohexyl]-1H-benzimidazol-5-yl)propanoic acid | 0.07 |
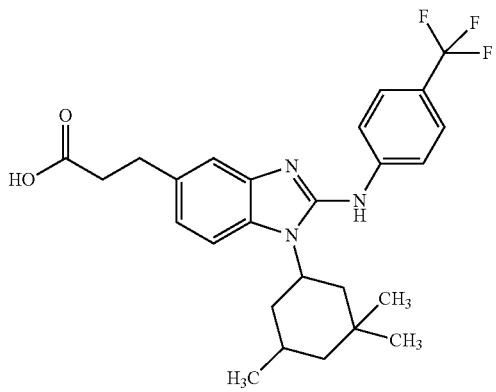 [SMILES: CC1CC(n2c(Nc3ccc(C(F)(F)F)cc3)nc3cc(CCC(=O)O)ccc32)CC(C)(C)C1]
| | |
|---|---|
| | 0.17 |
| (±) 3-(2-{[4-(Trifluoromethoxy)phenyl]amino}-1-[(cis)-3,3,5-trimethylcyclohexyl]-1H-benzimidazol-5-yl)propanoic acid | |
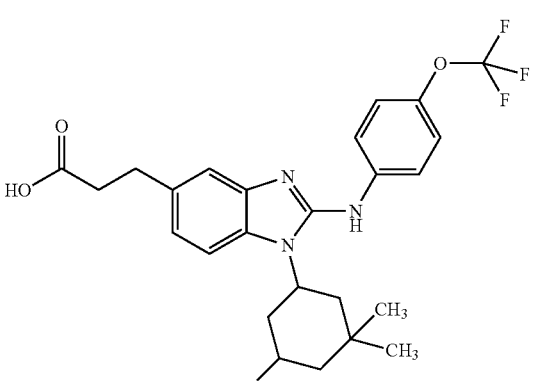
| | |
|---|---|
| (±) Methyl 3-(2-{[4-(propan-2-yl)phenyl]amino}-1-[(cis)-3,3,5-trimethylcyclohexyl]-1H-benzimidazol-5-yl)propanoate | 0.09 |
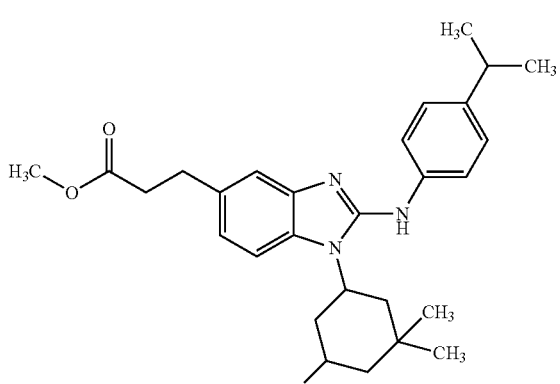

TABLE 3-continued

Inhibition of IDH1 R132H in the cellular assay

| Example | IDH1 R132H IC$_{50}$ [μM] |
|---|---|
| (±) Methyl 3-(2-{[4-(trifluoromethyl)phenyl]amino}-1-[(cis)-3,3,5-trimethylcyclohexyl]-1H-benzimidazol-5-yl)propanoate | 0.20 |
| (±) Methyl 3-(2-{[4-(trifluoromethoxy)phenyl]amino}-1-[(cis)-3,3,5-trimethylcyclohexyl]-1H-benzimidazol-5-yl)propanoate | 0.30 |

The invention claimed is:

1. A method for preparing methyl 3-(2-{[4-(trifluoromethoxy)phenyl]amino}-1-[(1R,5R)-3,3,5-trimethylcyclohexyl]-1H-benzimidazol-5-yl)propanoate:

comprising:
reacting methyl 3-(3-amino-4-{[(1R,5R)-3,3,5-trimethylcyclohexyl]amino}phenyl)propanoate-1,4-dioxane hydrochloride (1:1:2):

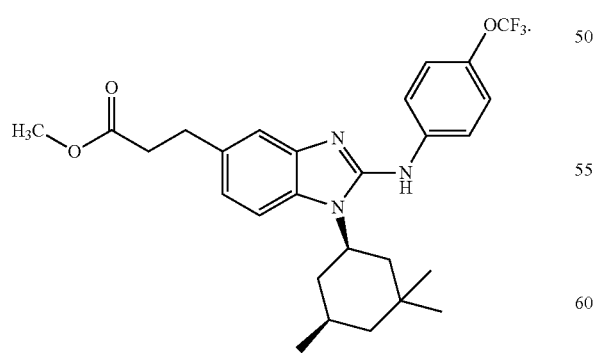

with 4-isothiocyanatophenyl trifluoromethyl ether:

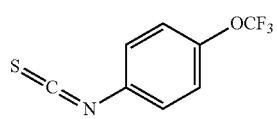 [SMILES: FC(F)(F)Oc1ccc(N=C=S)cc1]

to form methyl 3-(2-{[4-(trifluoromethoxy)phenyl]amino}-1-[(1R,5R)-3,3,5-trimethylcyclohexyl]-1H-benzimidazol-5-yl)propanoate.

2. The method according to claim 1, wherein the method comprises the following steps:
- (a) reacting methyl 3-(4-fluoro-3-nitrophenyl)propanoate with (1R,5R)-3,3,5-trimethylcyclohexanamine to give methyl 3-(3-nitro-4-{[(1R,5R)-3,3,5-trimethylcyclohexyl]amino}phenyl)propanoate;
- b) reducing methyl 3-(3-nitro-4-{[(1R,5R)-3,3,5-trimethylcyclohexyl]amino}phenyl)propanoate from step (a) to give methyl 3-(3-amino-4-[(1R,5R)-3,3,5-trimethylcyclohexyl]amino}phenyl)propanoate, and treating methyl 3-(3-amino-4-{[(1R,5R)-3,3,5-trimethylcyclohexyl]amino}phenyl)propanoate with a hydrochloric acid/dioxane mixture to obtain methyl 3-(3-amino-4-{[(1R,5R)-3,3,5-trimethylcyclohexyl]amino}phenyl)propanoate-1,4-dioxane hydrochloride (1:1:2); and
- (c) reacting methyl 3-(3-amino-4-{[(1R,5R)-3,3,5-trimethylcyclohexyl]amino}phenyl)propanoate-1,4-dioxane hydrochloride (1:1:2) from step (b) with 4-isothiocyanatophenyl trifluoromethyl ether to give methyl 3-(2-{[4-(trifluoromethoxy)phenyl]amino}-1-[(1R,5R)-3,3,5-trimethylcyclohexyl]-1H-benzimidazol-5-yl)propanoate.

3. The method according to claim 2, further comprising saponifying methyl 3-(2-{[4-(trifluoromethoxy)phenyl]amino}-1-[(1R,5R)-3,3,5-trimethylcyclohexyl]-1H-benzimidazol-5-yl)propanoate from step (c) to give 3-(2-{[4-(trifluoromethoxy)phenyl]amino}-1-[(1R,5R)-3,3,5-trimethylcyclohexyl]-1H-benzimidazol-5-yl)propanoic acid.

4. The method according to claim 3, wherein the saponification is effected by an aqueous sodium hydroxide solution in THF, the sodium hydroxide solution is subsequently neutralized with hydrochloric acid, and 3-(2-{[4-(trifluoromethoxy)phenyl]amino}-1-[(1R,5R)-3,3,5-trimethylcyclohexyl]-1H-benzimidazol-5-yl)propanoic acid is crystallized out from the solution by addition of isopropanol.

* * * * *